United States Patent [19]
Falk et al.

[11] Patent Number: 5,310,773
[45] Date of Patent: May 10, 1994

[54] PERFLUOROALKYL SUBSTITUTED HYDROXYPHENYLALKANOIC ESTER ANTIOXIDANTS AND STABILIZED COMPOSITIONS

[75] Inventors: Robert A. Falk, New City; Eduard K. Kleiner, Pound Ridge, both of N.Y.

[73] Assignee: Ciba-Geigy Corporation, Ardsley, N.Y.

[21] Appl. No.: 893,293

[22] Filed: Jun. 4, 1992

[51] Int. Cl.$^5$ .................. C07C 69/88; C07C 311/24; C07C 235/48; C08K 5/13; C08K 5/43; C08K 5/20

[52] U.S. Cl. .................................. 524/289; 560/67; 560/75; 524/167; 524/168; 524/219; 524/288

[58] Field of Search .................. 560/67, 75; 524/288, 524/289, 167, 168, 219; 252/404

[56] References Cited

U.S. PATENT DOCUMENTS

| | | | |
|---|---|---|---|
| 3,285,855 | 11/1966 | Dexter et al. | 524/289 |
| 3,422,059 | 1/1969 | Taylor et al. | 524/289 |
| 3,478,116 | 11/1969 | Smeltz | 528/308 |
| 3,642,868 | 2/1972 | Dexter et al. | 560/75 |
| 3,944,594 | 3/1976 | Kleiner et al. | 560/75 |
| 4,046,944 | 9/1977 | Mueller et al. | 524/317 |
| 4,049,713 | 9/1977 | Spivack | 524/291 |
| 4,058,502 | 11/1977 | Dexter et al. | 524/289 |
| 4,071,497 | 1/1978 | Dexter et al. | 524/289 |
| 4,898,981 | 2/1990 | Falk et al. | 568/28 |
| 4,946,992 | 8/1990 | Falk et al. | 568/29 |
| 5,045,624 | 9/1991 | Falk et al. | 528/70 |
| 5,068,397 | 11/1991 | Falk et al. | 560/152 |

FOREIGN PATENT DOCUMENTS 2664268 1/1992 France.
1103145 2/1968 United Kingdom.

OTHER PUBLICATIONS

Bull. Chem. Soc. Jpn. 57, 3361–3362 (1984).

*Primary Examiner*—Veronica P. Hoke
*Attorney, Agent, or Firm*—Luther A. R. Hall

[57] ABSTRACT

Perfluoroalkyl substituted neopentyl alcohols can be reacted with substituted hydroxphenylalkanoic esters to form perfluoroalkyl containing hydroxyphenylalkanoic ester antioxidants. The perfluoroalkyl substituted hindered hydroxyphenyl alkanoates are stablizers which confer superior processing stability to polymers processed at elevated temperatures such as polypropylene, as well as protecting said polymers from thermal and oxidative degradation.

28 Claims, No Drawings

PERFLUOROALKYL SUBSTITUTED HYDROXYPHENYLALKANOIC ESTER ANTIOXIDANTS AND STABILIZED COMPOSITIONS

The instant invention pertains to perfluoroalkyl substituted phenolic antioxidants useful for the stabilization of organic material against oxidative and thermal deterioration.

BACKGROUND OF THE INVENTION

The invention relates to perfluoroalkyl substituted antioxidants and their use to impart exceptional antioxidant properties to polymeric substrate which subject to severe environmental conditions. Fluorochemical additives has demonstrated the unique ability to modify the surface properties of polymers by adsorption at the polymer/air interface even when used at very low levels. This has been demonstrated by measurements of reduced wettability and decreased friction. Adsorption may occur at the polymer/air interface during the formation of the polymer surface. There is also evidence that certain fluorinated additive molecules are sufficiently mobile in the solid polymer to reach and repair the surface by diffusion and selective adsorption. Thus, they have the unique ability to self-heal, i.e. the molecules from the interior of the polymer can migrate to and repair an additive deficient surface. Fluorochemicals can inherently retain these unique migrating properties while maintaining the high molecular weight necessary to minimize volatility. This application for fluorochemical antioxidants has not hitherto been described. Because of the high costs of fluorochemicals, the use level of the derived fluorochemical is an important consideration. It is anticipated that the subject fluorinated antioxidants will function as synergists and as minor additives in combination with standard antioxidants. Major use areas are fiber, films, high density polyethylene and automative plastics. Inexpensive butylated hydroxytoluenes are sufficient for many low temperature applications, but when polymers are processed and fabricated at elevated temperatures, less volatile high molecular weight additives which have a lower propensity to discolor are required.

2,4-bis(tertbutyl)-6-(heptafluoropropyl)-phenol has been reported in Bull. Chem. Soc. Jpn, 57 (11), 3361 (1984). Said compound has not been suggested as an antioxidant and it would be much too volatile for use as a high temperature antioxidant in any event.

DETAILED DISCLOSURE

This invention pertains to perfluoroalkyl containing esters of hindered hydroxyphenylalkanoic acids and to organic materials normally subject to oxidative, thermal and light induced deterioration stabilized with said ester compounds.

More specifically, the instant invention is to a compound of formula I, II or III

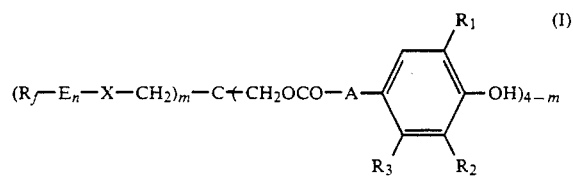

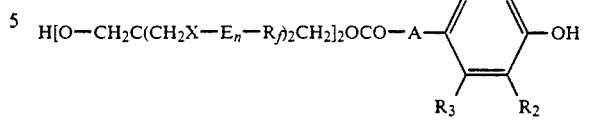

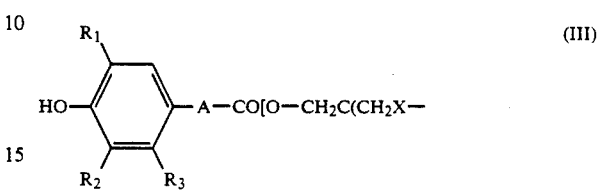

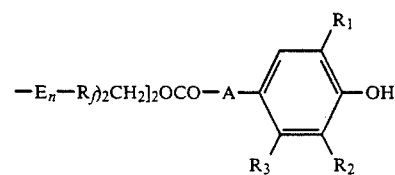

wherein $R_1$ and $R_2$ are independently alkyl 1 to 12 carbon atoms, cycloalkyl of 5 to 12 carbon atoms, said cycloalkyl substituted by alkyl of 1 to 4 carbon atoms, phenyl, phenylalkyl of 7 to 15 carbon atoms or said phenyl or said phenylalkyl substituted on the phenyl ring by alkyl of 1 to 4 carbon atoms, by —OH, by methoxy or by a mixture thereof, $R_3$ is hydrogen or alkyl of 1 to 4 carbon atoms, or $R_2$ and $R_3$ together are tetramethylene, A is a direct bond or a straight or branched chain alkylene of 1 to 8 carbon atoms, $R_f$ is independently a straight or branched chain perfluoroalkyl of 1 to 14 carbon atoms, perfluoroalkyl of 2 to 6 carbon atoms substituted by perfluoroalkyl of 2 to 6 carbons atoms, or an oligo(hexafluoropropene oxide) terminal group, n is 1 or 0, when n is 1, E is independently a branched or straight chain alkylene of 1 to 10 carbon atoms or said alkylene interrupted by one to three groups selected from the group consisting of —NR—, —O—, —S—, —SO₂—, —COO—, —OOC—, —CONR—, —NRCO—, —SO₂NR—, —NRSO₂—, or terminated at the $R_f$ end with —CONR— or —SO₂NR—, where $R_f$ is attached to the carbon or sulfur atom, and X is —S—, —O—, —SO₂—, —NR—, or —COO—, or when n is 0, X is a direct bond, —CONR— or —SO₂NR—, where $R_f$ is attached to the carbon or sulfur atom, and where R is independently hydrogen, alkyl of 1 to 6 carbon atoms or hydroxyalkyl of 2 to 6 carbon atoms, and m is 1, 2 or 3.

The acids from which the instant perfluoroalkyl substituted antioxidants are derived have the general formula (IV):

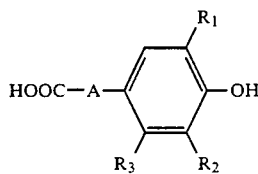

(IV)

wherein $R_1$, $R_2$, $R_3$ and A are as defined above.

The $R_1$, $R_2$ and $R_3$ groups can be, for example, methyl, ethyl, propyl, isopropyl, sec-butyl, tert-butyl, tert-amyl, hexyl, 2-ethylhexyl, octyl, tert-octyl, decyl or dodecyl. $R_1$ and $R_2$ are preferably independently methyl or a branched alkyl of 1 to 8 carbon atoms such as isopropyl, tert-butyl, tert-amyl or tert-octyl. Particularly preferred, $R_1$ and $R_2$ are the same and are each tert-butyl.

$R_1$ and $R_2$ are, for example benzyl, 2-phenylethyl, 1-phenylethyl, 3,5-dimethyl-4-hydroxybenzyl, hydroxybenzyl or methoxybenzyl; or cyclohexyl.

$R_3$ is preferably hydrogen or methyl, most preferably hydrogen.

A is a direct bond or a straight or branched alkylene having 1 to 8 carbon atoms, typically methylene, ethylene, 1,2-propylene, trimethylene, 1,1-butylidene, 2-methyl-1,1-propylidene and 1,1-octylidene. Preferably A is a direct bond or a straight chain alkylene of 1 to 3 carbon atoms, that is, methylene, ethylene and trimethylene. Most preferably A is ethylene.

The novel heteroatom containing $R_f$-neopentyl alcohols from which the instant perfluoroalkyl containing antioxidants are prepared are described in U.S. Pat. Nos. 4,898,981, 4,946,992, 5,045,624 and 5,068,397. These alcohols have the formula V or VI:

$$(R_f-E_n-X-CH_2)_m-C-(CH_2OH)_{4-m} \quad (V)$$

$$H[O-CH_2C(CH_2X-E_n-R_f)_2CH_2]_2-OH \quad (VI)$$

wherein $R_f$ is independently a straight or branched chain perfluoroalkyl of 1 to 12 carbon atoms, perfluoroalkyl of 2 to 6 carbon atoms substituted by perfluoroalkoxy of 2 to 6 carbon atoms, or an oligo(hexafluoropropene oxide) terminal group, and n=1 or 0, and when n=1, E is independently a branched or straight chain alkylene of 1 to 10 carbon atoms or said alkylene interrupted by one to three groups selected from the group consisting of —NR—, —O—, —S—, —SO$_2$—, —COO—, —OOC—, —CONR—, —NRCO—, —SO$_2$NR—, —NRSO$_2$—, or terminated at the $R_f$ end with —CONR— or —SO$_2$NR—, where $R_f$ is attached to the carbon or sulfur atom, and X is —S—, —O—, —SO$_2$—, —NR—, or —COO—, and when n=0, X is a direct bond, —CONR— or —SO$_2$NR—, where $R_f$ is attached to the carbon or sulfur atom, and where R is independently hydrogen, alkyl of 1 to 6 carbon atoms or hydroxyalkyl of 2 to 6 carbon atoms.

It is understood that the $R_f$ group usually represents a mixture of perfluoroalkyl moieties. When the $R_f$ group is identified as having a certain number of carbon atoms, said $R_f$ group also usually concomitantly contains a small fraction of perfluoroalkyl groups with lower carbon atoms and a small fraction of perfluoroalkyl groups with higher carbon atoms. Commonly the perfluoroalkyl moiety is a mixture of $C_4F_9$—, $C_6F_{13}$—, $C_8F_{17}$—, $C_{10}F_{21}$—, $C_{12}F_{25}$—, and $C_{14}F_{29}$—.

Preferably the instant compounds are those where $R_f$ is perfluoroalkyl of 6 to 12 carbon atoms or perfluoroalkyl of 2 to 6 carbon atoms substituted by perfluoroalkoxy of 2 to 6 carbon atoms, E is alkylene of 2 to 6 carbon atoms, —CONHCH$_2$CH$_2$—, —CH$_2$CH$_2$N(CH$_3$)CH$_2$CH$_2$—, —CH$_2$CH$_2$SO$_2$NHCH$_2$CH$_2$— or —SO$_2$NHCH$_2$CH$_2$—, X is —S—, —SO$_2$— or —O—.

Most preferred are those compounds of formula I where $R_f$ is perfluoroalkyl of 6 to 12 carbon atoms, E is ethylene, and X is S, i.e.,

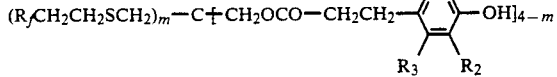

Compounds wherein m is 2 or 3 are most preferred.

The esters of this invention are prepared by common esterification procedures from a suitable perfluoroalkyl substituted neopentyl alcohol of the formula V or VI and an acid of the formula IV, or an acid halide or acid anhydride thereof. The perfluoroalkyl esters can also be prepared from the lower alkyl esters, especially the methyl ester of the above represented compounds, by transesterification. The carboxylic acid derivatives which are converted to the compounds of this invention are made as described in U.S. Pat. No. 4,049,713. Most of the 2,6-dialkylated and 2,3,6-trialkylated phenols contemplated for use as starting materials to make the compounds of this invention are known compounds which are available commercially. If not available, the synthesis of these starting phenols have been disclosed or described in U.S. Pat. No. 4,049,713.

The perfluoroalkyl substituted hindered hydroxyphenylalkanoates of this invention not only have superior stabilizing properties, but also exhibit resistance to gas fading in polymeric substrates such as polypropylene multifilament knitted cloth to a high degree not shown by other antioxidants. In addition, the stabilizers of this invention confer superior processing stability to polymers, such as polypropylene, as well as being extraction resistant. This combination of properties is particularly important for textiles fabricated from synthetic polymers.

Another aspect of the instant invention is to a stabilized composition which comprises (a) an organic material subject to thermal and oxidative degradation, and (b) an effective stabilizing amount of a compound of formula I, II or III as described above.

Substrates in which the compounds of this invention are particularly useful are the polyolefins, such as polyethylene and polypropylene. Polypropylene is particularly well stabilized by the instant compounds during processing.

While the instant compounds of formula I, II or III are quite effective process stabilizers for polyolefins when used alone, compositions which also contain another phenolic antioxidant are also extremely well stabilized during processing by this combination of process stabilizers.

In general polymers which can be stabilized include
1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.
8. Polymers which are derived from $\alpha,\beta$-unsaturated acids and derivatives thereof, such as polyacrylates and polymethacrylates, polyacrylamide and polyacrylonitrile.
9. Copolymers from the monomers mentioned under 8) with each other or with other unsaturated monomers, such as, for instance, acrylonitrile/butadiene, acrylonitrile/alkyl acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.
30. Polysiloxanes such as the soft, hydrophilic polysiloxanes described, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer.
33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1 Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |

| | |
|---|---|
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example,
diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbometh oxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methylindoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone).

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)-phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphonites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N- hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)-butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-trazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylene-bis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]undecane)-diethyl] 1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]undecane)-diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), and bis(1-octyloxy-2,2,6,6-tetramethylpiperidin-4-yl) sebacate.

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis-(amino-2,2,6,6-tetramethylpiperidine) or N,N',N'',N'''-tetrakis[(4,6-bis(butyl-(2,2,6,6-tetramethyl-piperidin-4-yl)amino)-s-triazine-2-yl]1,10-diamino-4,7-diazadecane or bis(1-octyloxy-2,2,6,6-tetramethylpiperidin-4-yl) sebacate.

The lubricating oil may be a mineral oil, a synthetic oil or any mixture of such oils. Mineral oils are preferred and examples of these include paraffinic hydrocarbon oils e.g. a mineral oil having a viscosity of 46 mm$^2$/s at 40° C.; "150 Solvent Neutral" a solvent refined neutral mineral oil having a viscosity of 32 mm$^2$/s at 40 C.; and "solvent bright-stocks", a high boiling residue from the process of refining mineral oil, and having a viscosity of 46 mm$^2$/s at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula: G$_1$-OCC-alkylene-COOG$_2$ wherein "alkylene" denotes an alkylene residue having from 2 to 14 carbon atoms and G$_1$ and G$_2$ are the same or different and each is an alkyl group having from 6 to 18 carbon atoms. Tri-esters which are of use as lubricating oil base stocks are those derived from trimethylolpropane and $C_6$–$C_{18}$ mono-carboxylic acids or mixtures thereof, whereas suitable tetra-esters include those derived from pentaerythritol and a $C_6$–$C_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

Examples of phenolic antioxidants

1. Alkylated Monophenols 2,6-Di-tert-butyl-4-methylphenol, 2,6-di-tert-butylphenol, 2-tert-butyl-4,6-dimethylphenol,2,6-di-tert-butyl-4-ethyl-phenol, 2,6-di-tert-butyl-4-n-butylphenol, 2,6-di-tert-butyl-4-i-butylphenol, 2,6-di-cyclopentyl-4-methylphenol, 2-(β-methylcyclohexyl)4,6-dimethyl-phenol, 2,6-di-octa-decyl-4-methylphenol, 2,4,6-tri-cyclohexylphenol, 2,6-di-tert-butyl-4-methoxymethyl-phenol, o-tert-butylphenol.

2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers 2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methyl-phenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexyl-phenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-(α-methylbenzyl-4-nonylphenol), 2,2'-methylene-bis-(6-(α,α-di-methylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl-2-hydroxy-benzyl)-4-methyl-phenol, 1,1,3-tris-(5-tert-butyl-4-hydroxy-2-methyl-phenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, bis-hydroxyethyl-oxalic acid diamide.

8. Esters of β-(5-tert-butyl-4-hydroxy-3-methylphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, di-hydroxyethyl-oxalic acid diamide.

9. Amides of β-(3,5-Di-tert-butyl-4-hydroxyphenyl)-propionic acid for example N,N'-Bis-(3,5-di-tert-butyl-4-hydroxy-phenylpropionyl)-hexamethylene-diamine, N,N'-bis(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of amine antioxidants

N,N'-Di-isopropyl-p-phenylenediamine, N,N'-di-sec.-butyl-p-phenylenediamine, N,N'-bis(1,4-dimethylpentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylene-diamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldi-phenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4- nonanoylamino-phenol, 4-dodecanoyl-amino-phenol, 4-octadecanoyl-amino-phenol, di-(4-methoxy-phenyl)-amine, 2,6-di-tert-butyl-4-dimethyl-amino-methyl-phenol, 2,4'-diamino-diphenylmethane, 4,4'-diaminodiphenyl-methane, N,N,N',N'-tetramethyl-4,4'-diamino-diphenylmethane, 1,2-di-(phenylamino)-ethane, 1,2-di-[2-methyl-phenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, N-allyl-phenothiazine, tert-octylated phenothiazine, 3,7-di-tert-octylphenothiazine.

Examples for other antioxidants

Aliphatic or aromatic phosphites, esters of thiodipropionic acid or of thiodiacetic acid, or salts of dithiocarbamic or dithiophosphoric acid.

Examples of metal passivators, for example for copper, are: Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole, salicyclidene-propylene-diamine and salicyclamino-guanidine and salts thereof, 1,2,4-triazole and N,N'-disubstituted aminomethyl triazoles of formula

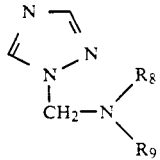

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of rust inhibitors are: a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.

b) Nitrogen-containing compounds, e.g. I. Primary, secondary or tertiary aliphatic or cycloaliphatic amines and amine-salts of organic and inorganic acids, e.g. oil-soluble alkyl-ammonium carboxylates II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonylnaphthalene-n-sulfonates, calcium petroleum sulfonates.

e) Derivatives of gamma-alkoxypropylamines described in Japanese Patent Publication No. 15783/1973; and f) Salts having the formula $Y-NH_3-R_{10}CO_2-$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y-NH_2$ with an acid $R_{10}CO_2H$, as disclosed in DE-OS 3437 876 (German Offenlegungsschrift).

g) Compounds having the formula

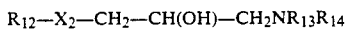

in which $X_2$ is $-O-$, $-S-$, $-SO_2-C(O)-O-$ or $-N(Rd)$ in which $R_{12}$ is H or $C_1-C_{12}$alkyl, $R_{13}$ is unsubstituted $C_1-C_4$alkyl or $C_2-C_5$alkyl substituted by one to three hydroxyl groups, $R_{14}$ is hydrogen, unsubstituted $C_1-C_4$alkyl or $C_2-C_5$alkyl substituted by one to three hydroxyl groups provided that at least one of $R_{13}$ and $R_{14}$ is hydroxy-substituted, and $R_{12}$ is $C_2-C_{20}$alkyl $-CH_2-CH(OH)-CH_2NR_{13}R_{14}$ or $R_{12}$ is $C_2-C_{18}$alkenyl, $C_2-C_3$alkynyl or $C_5-C_{12}$cycloalkyl provided that, when $X_2$ is $-O-$ or $-C(O)-O-$, $R_{12}$ is branched $C_4-C_{20}$alkyl. These compounds are described in GB Patent Specification 2172284A.

h) Compounds having the formula:

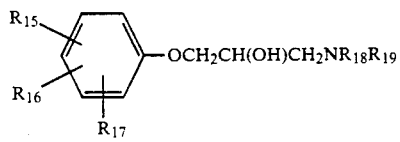

in which $R_{15}$, $R_{16}$, $R_{17}$ are, independently, hydrogen, $C_1-C_{15}$alkyl, $C_5-C_{12}$cycloalkyl, $C_6-C_{15}$aryl or $C_7-C_{12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each $-CH_2CH_2OH$, $R_{15}$ and $R_{16}$ are not simultaneously hydrogen and $R_{17}$ is not pentyl. These compounds are described in EP Patent specification 0 252 007.

Examples of viscosity-index improvers are: Polyacrylates, polymethacrylates, vinylpyrrolidone/methacrylate-copolymers, polyvinylpyrrolidones, polybutanes, olefin-copolymers, styrene/-acrylate-copolymers, polyethers.

Examples of pour-point depressants are: Polymethacrylates, alkylated naphthalene derivatives.

Examples of dispersants/detergents are: Polybutenyl-succinic acid-amides or -imides, polybutenyl-phosphonic acid derivatives, basic magnesium-, calcium-, and bariumsulfonates and -phenolates.

Examples of anti-wear additives and extreme pressure additives are: Sulphur- and/or phosphorus- and/or halogen-containing compounds e.g. sulphurised vegetable oils, zinc dialkyldithiophosphates, tritolylphosphate, chlorinated paraffins, alkyl- and aryldi- and trisulphides, triphenylphosphorothionate.

The following examples are illustrative of the invention, but are not meant to limit the scope of said invention in any manner whatsoever. In said examples, parts are by weight unless otherwise indicated.

EXAMPLE 1

2,2-Bis(1,1,2,2-tetrahydroperfluorooctylthiomethyl)-1,3-propanediyl Bis(3,5-di-tert-butyl-4-hydroxyhydrocinnamate)

2,2-Bis(1,1,2,2-tetrahydroperfluorooctylthiomethyl)-1,3-propanediol (20.0 gm, 0.021 mol) and methyl 3,5-di-tert-butyl-4-hydroxyhydrocinnamate (13.0 gm, 0.044 mol) are reacted under nitrogen at 115° C. overnight in the presence of a catalytic amount of lithium hydride. A small amount of acetic acid is added to precipitate the lithium acetate which is removed by filtration after dissolving the crude product in petroleum ether. The solvent is evaporated to yield 28.2 gm of a yellow viscous crude product (94.3% of theory). Purification is accomplished via column chromatography using neutral alumina as the stationary phase and eluting with a 3 part toluene, 5 part hexane solvent. This yields the title compound as a pale yellow solid melting at 77°–79° C. The purity of the compound is affirmed by thin layer chromatography.

NMR shows proton resonances at 1.42 ppm, 36 protons, tert-butyl; 2.2–3.0 ppm, 20 protons, unassigned; 4.11 ppm, 4 protons, ester —$CH_2$—; 5.12 ppm, 2 protons —OH; 7.02 ppm, 4 protons, aromatic.

Analysis: Calcd for $C_{55}H_{66}F_{26}O_6S_2$: C, 47.8; H, 4.8; F, 35.8. Found: C, 47.9; H, 4.9; F, 35.6.

EXAMPLE 2

2,2-Bis(1,1,2,2-tetrahydroperfluorodecylthiomethyl)-1,3-propanediyl
Bis(3,5-di-tert-butyl-4-hydroxyhydrocinnamate)

2,2-Bis(1,1,2,2-tetrahydroperfluorodecylthiomethyl)-1,3-propanediol (20.0 gm, 0.018 mol) and methyl 3,5-di-tert-butyl-4-hydroxyhydrocinnamate (10.9 gm, 0.037 mol) are reacted under nitrogen at 115° C. overnight in the presence of a catalytic amount of lithium hydride. A small amount of acetic acid is added to precipitate lithium acetate which is subsequently removed by filtration after dissolving the crude product in hexane. The solvent is evaporated off to yield 27.8 gm of a yellow viscous crude product (96.5% of theory). Purification is accomplished via column chromatography using neutral alumina as the stationary phase and eluting with a 3 part toluene, 5 part hexane solvent. This yields the title compound as a pale yellow solid melting at 93°–95° C. The purity of the product is affirmed by thin layer chromatography.

NMR shows proton resonances at 2.08 ppm, 36 protons, tert-butyl; 2.1–3.0 ppm, 20 protons, unassigned; 4.1 ppm, 4 protons, ester —$CH_2$—; 5.03 ppm, 2 protons, —OH; 6.98 ppm, 4 protons, aromatic.

Analysis: Calcd for $C_{59}H_{66}F_{34}O_6S_2$: C, 44.8; H, 4.2; F, 40.9; S, 4.1. Found: C, 44.7; H, 4.2; F, 40.5; S, 4.1.

EXAMPLE 3

3-(1,1,2,2-Tetrahydroperfluorooctylthio)-2,2-bis(1,1,2,2-tetrahydroperfluorooctylthiomethyl)-1-propyl 3,5-Di-tert-butyl-4-hydroxyhydrocinnamate 3-(1,1,2,2-Tetrahydroperfluorooctylthio)-2,2-bis(1,1,2,2-tetrahydroperfluorooctylthiomethyl)-1-propanol (22.0 gm, 0.018 mol) and methyl 3-(3,5-di-tert-butyl-4-hydroxyhydrocinnamate (7.9 gm, 0.027 mol) are reacted under nitrogen in the presence of a catalytic amount of lithium hydride (0.014 gm, 0.0018 mol) at 115° C. for twenty hours. At this time, GLC indicates little product conversion so additional lithium hydride is added. The reaction is run for four more hours. The temperature is then raised to 140°–150° C. and another dash of lithium hydride is added. The reaction is then to run for 23 additional hours. A substantial amount of product is now evident by GLC. Heptane is then added and the lithium catalyst is precipitated as lithium acetate by the addition of acetic acid. The solution is filtered, and the heptane stripped off. The title compound is purified via flash chromatography, followed by thin layer chromatography (3:1 ratio of hexane to isopropyl acetate). The solvent used in the flash chromatography is 95:5 heptane: ethyl acetate. Twenty-five grams of this mixture is used to dissolve the product for application to the column. The solvent is then run through the column and the fractions collected. Combined product fractions are evaporated, leaving 4.4 gm of the title compound as an off white powder melting at 77°–79° C. The product is analyzed as having 94% purity by GLC.

NMR shows proton resonances at 1.45 ppm, 18 protons, tert-butyl; 2.2–2.5 ppm, 6 protons, $R_fCH_2$; 2.6–2.9 ppm, 2 protons, complex; -$CH_2$-Ar; 2.75 ppm, 12 protons; $CH_2S$; 4.1 ppm, 2 protons; $CH_2O_2C$; 5.1 ppm, 1 proton; -OH; 7.0 ppm, 2 protons, aromatic.

Analysis: Calcd for $C_{46}H_{45}F_{39}O_3S_3$: C, 37.3; F, 50.0; H, 3.0. Found: C, 37.2; F, 49.9; H, 3.0.

EXAMPLE 4

2,2,6,6-Tetrakis(1,1,2,2-tetrahydroperfluorooctylthiomethyl)-4-oxa-1,7-heptanediyl
Bis(3,5-di-tert-butyl-4-hydroxyhydrocinnamate)

and

7-Hydroxy-2,2,6,6-tetrakis(1,1,2,2-tetrahydroperfluorooctylthiomethyl)4-oxa-1-heptyl
3,5-Di-tert-butyl-4-hydroxyhydrocinnamate Tetrakis(1,1,2,2-tetrahydroperfluorooctylthiomethyl)-4-oxa-1,7-heptanediol (22.0 gm, 0.013 mol) and methyl 3,5-di-tert-butyl-4-hydroxyhydrocinnamate (4.3 gm, 0.015 mol) are reacted with lithium hydride as catalyst (0.02 gm, 0.002 mol) under nitrogen for six hours at 140° C. The reaction is run for fifteen hours and then additional methyl 3,5-di-tert-butyl-4-hydroxyhydrocinnamate (2.0 gm) is added. The reaction is then run for an additional twenty-four hours. Purification of the product is accomplished via flash chromatography using 9:1 hexane: ethyl acetate. Thin layer chromatography is used to determine the presence of the desired product in each fraction. Two major products are apparent. One fraction is evaporated to yield a product which is then crystallized twice from methanol. The resultant white powder melting at 54°–55° C. is 90.5% pure by GLC, and and is the monoester title compound. The diester is made at the same time as the monoester, and can also be isolated by chromatography.

Analysis: Calcd for $C_{59}H_{58}F_{52}O_5S_4$: C, 36.1; H, 3.0; F, 50.3. (monoester) Found: C, 35.9; H, 2.9; F, 49.7.

EXAMPLES 5–15

Using the general methods set forth in Examples 1–4, the following fluorinated compounds of this invention are prepared.

| Example | Perfluoroalkyl Antioxidants |
| --- | --- |
| 5 | $(CF_3CF_2CH_2SCH_2)_2C(CH_2\text{-}M)_2$ |
| 6 | $(C_6F_{13}(CH_2)_4SO_2CH_2)_2C(CH_2\text{-}M)_2$ |
| 7 | $(C_8F_{17}SO_2NHCH_2CH_2OCH_2)_2C(CH_2\text{-}T)_2$ |
| 8 | $(C_8F_{17}CH_2CH_2SO_2NHCH_2CH_2SCH_2)_2C(CH_2\text{-}T)_2$ |
| 9 | $(C_7F_{15}CONHCH_2CH_2CH_2SCH_2)_2C(CH_2\text{-}Q)_2$ |
| 10 | $(CF_3CF_2CH_2OCH_2)_3CCH_2\text{-}Y$ |
| 11 | $(C_6F_{13}(CH_2)_4SO_2CH_2)_3CCH_2\text{-}G$ |
| 12 | $(C_8F_{17}SO_2N(C_2H_5))_3CCH_2\text{-}J$ |
| 13 | $(C_8F_{17}SO_2NHCH_2CH_2OCH_2)_3CCH_2\text{-}Q$ |
| 14 | $(C_8F_{17}CH_2CH_2SO_2NHCH_2CH_2OCH_2)_3CCH_2\text{-}M$ |
| 15 | $(C_8F_{17}CH_2CH_2OCH_2)_3CCH_2\text{-}L$ | wherein
M is 3,5-di-tert-butyl-4-hydroxyhydrocinnamoyloxy;

T is 3-methyl-5-tert-butyl-4-hydroxyhydrocinnamoyloxy;
Q is 2,3-dimethyl-5-tert-butyl-4-hydroxyhydrocinnamoyloxy;
Y is 3,5-di-tert-butyl-4-hydroxybenzoyloxy;
G is 3,5-di-tert-butyl-4-hydroxyphenylacetoxy;
J is 3,5-diisopropyl-4-hydroxyhydrocinnamoyloxy; and
L is 3,5-dimethyl-4-hydroxy-benzoyloxy.

EXAMPLE 16

Stabilization of Polypropylene

100 Parts of polypropylene powder (PROFAX® 6501, Hercules) containing 0.1% by weight of calcium stearate are homogeneously mixed with the test antioxidant additive. The resultant mixture is extruded in a single pass in a single screw extruder at a maximum of 127° C. (or 138° C. temperature of the discharge zone) and 100 rpm, and then granulated. The resultant polymer is molded in a press with a surface temperature of 127° C. to plates of 1 mm thickness. Strips 1 cm in width and 8.5 cm in length are punched out of these plates. Several such strips from each plate are hung in a circulating air oven which has been heated to 65° C. The strips are then observed at regular intervals. The time in hours elapsed till the sample strips become brittle and fragile to the touch is noted as the time to failure.

| Stabilizer Compound of Example* | Concentration % by weight | Number of Hours to Failure |
|---|---|---|
| 1 | 0.2 | 1740 |
| 2 | 0.2 | 1050 |

These data indicate that the instant compounds provide excellent antioxidant protection to polypropylene.

EXAMPLE 17

Stabilization of Polypropylene

The general procedure of Example 16 is repeated where a portion of a non-fluorinated antioxidant is replaced with a fluorinated antioxidant of the instant invention.

| Stabilizer Compound of Example* | Concentration % by weight | Number of Hours to Failure |
|---|---|---|
| AOA | 0.2 | 1240 |
| AOA plus 1 | 0.18 0.02 | 1440 |
| AOA plus 2 | 0.18 0.02 | 1320 |
| AOB | 0.2 | 126 |
| AOB plus 1 | 0.16 0.04 | 369 |
| AOB plus 2 | 0.16 0.04 | 292 |

*AOA is neopentanetetrayl tetrakis(3,5-di-tert-butyl-4-hydroxyhydrocinnamate).
AOB is n-octadecyl 3,5-di-tert-butyl-4-hydroxyhydrocinnamate.

These data indicate that the use of a conventional non-fluorinated antioxidant along with a small synergistic amount of a fluorinated antioxidant of this invention provides greatly improved antioxidant protection to polypropylene.

What is claimed is:

1. A compound of formula I, II or III

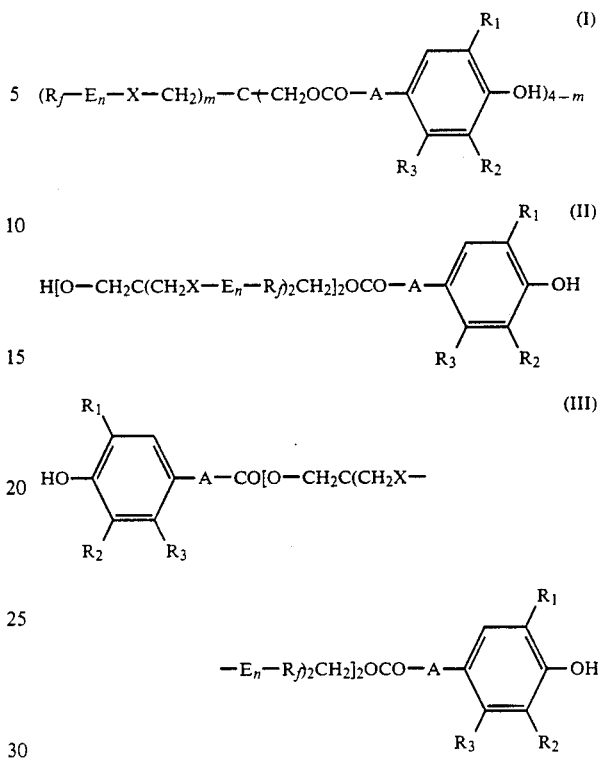

wherein
$R_1$ and $R_2$ are independently alkyl of 1 to 12 carbon atoms, cycloalkyl of 5 to 12 carbon atoms, said cycloalkyl substituted by alkyl of 1 to 4 carbon atoms, phenyl, phenylalkyl of 7 to 15 carbon atoms or said phenyl or said phenylalkyl substituted on the phenyl ring by alkyl of 1 to 4 carbon atoms, by —OH, by methoxy or by a mixture thereof,
$R_3$ is hydrogen or alkyl of 1 to 4 carbon atoms, or
$R_2$ and $R_3$ together are tetramethylene,
A is a direct bond or a straight or branched chain alkylene of 1 to 8 carbon atoms,
$R_f$ is independently a straight or branched chain perfluoroalkyl of 1 to 14 carbon atoms, perfluoroalkyl of 2 to 6 carbon atoms substituted by perfluoroalkoxy of 2 to 6 carbon atoms, or an oligo(hexafluoropropene oxide) terminal group,
n is 1 or 0,
when n is 1, E is independently a branched or straight chain alkylene of 1 to 10 carbon atoms or said alkylene interrupted by one to three groups selected from the group consisting of —NR—, —O—, —S—, —SO$_2$—, —COO—, —OOC—, —CONR—, —NRCO—, —SO$_2$NR—, —NRSO$_2$—, or terminated at the $R_f$ end with —CONR— or —SO$_2$NR—, where $R_f$ is attached to the carbon or sulfur atom, an X is —S—, —O—, —SO$_2$—, —NR—, or —COO—, or
when n is 0, X is a direct bond, —CONR— or —SO$_2$NR—, where $R_f$ is attached to the carbon or sulfur atom, and where R is independently hydrogen, alkyl of 1 to 6 carbon atoms or hydroxyalkyl of 2 to 6 carbon atoms, and
m is 1, 2 or 3.

2. A compound according to claim 1 wherein $R_1$ and $R_2$ are independently methyl or a branched alkyl of 1 to 8 carbon atoms.

3. A compound according to claim 2 wherein $R_1$ and $R_2$ are the same and are each tert-butyl.

4. A compound according to claim 1 wherein $R_3$ is hydrogen or methyl.

5. A compound according to claim 4 wherein $R_3$ is hydrogen.

6. A compound according to claim 1 wherein A is a direct bond or an alkylene of 1 to 3 carbon atoms.

7. A compound according to claim 6 wherein A is ethylene.

8. A compound according to claim 1 wherein $R_f$ is perfluoroalkyl of 6 to 12 carbon atoms or perfluoroalkyl of 2 to 6 carbon atoms substituted by perfluoroalkoxy of 2 to 6 carbon atoms, E is alkylene of 2 to 6 carbon atoms, —CONHCH$_2$CH$_2$—, CH$_2$CH$_2$N(CH$_3$)CH$_2$CH$_2$—, —CH$_2$CH$_2$SO$_2$NHCH$_2$CH$_2$— or SO$_2$NHCH$_2$CH$_2$—, X is —S—, —SO$_2$— or —O—.

9. A compound according to claim 8 of formula I, wherein $R_f$ is perfluoroalkyl of 6 to 12 carbon atoms, E is ethylene, and X is S.

10. A compound according to claim 1 wherein m is 2 or 3.

11. The compound according to claim 1 which is
2,2-bis(1,1,2,2-tetrahydroperfluorooctylthiomethyl)-1,3-propanediyl bis(3,5-di-tert-butyl-4-hydroxyhydrocinnamate);
2,2-bis(1,1,2,2-tetrahydroperfluorodecylthiomethyl)-1,3-propanediyl bis(3,5-di-tert-butyl-4-hydroxyhydrocinnamate);
3-(1,1,2,2-tetrahydroperfluorooctylthio)-2,2-bis(1,1,2,2-tetrahydroperfluorooctylthiomethyl)-1-propyl 3,5-di-tert-butyl-4-hydroxyhydrocinnamate;
2,2,6,6-tetrakis(1,1,2,2-tetrahydroperfluorooctylthiomethyl)-4-oxa-1,7-heptanediyl bis(3,5-di-tert-butyl-4-hydroxyhydrocinnamate); or
7-hydroxy-2,2,6,6-tetrakis(1,1,2,2-tetrahydroperfluorooctylthiomethyl)4-oxa-1-heptyl 3,5-di-tert-butyl-4-hydroxyhydrocinnamate.

12. A stabilized composition which comprises
(a) an organic material subject to thermal and oxidative degradation which is selected from the group consisting of a polymer, a wax, an oil, a fat and a lubricant, and
(b) an effective stabilizing amount of a compound of formula I, II or III

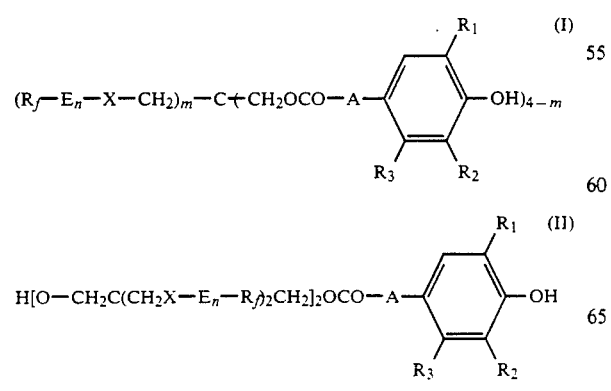

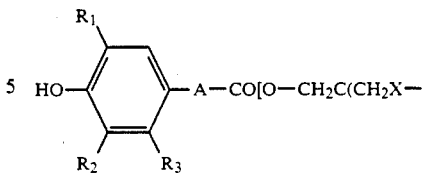

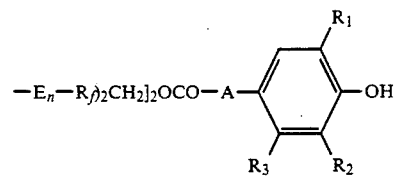

wherein
$R_1$ and $R_2$ are independently alkyl of 1 to 12 carbon atoms, cycloalkyl of 5 to 12 carbon atoms, said cycloalkyl substituted by alkyl of 1 to 4 carbon atoms, phenyl, phenylalkyl of 7 to 15 carbon atoms or said phenyl or said phenylalkyl substituted on the ring by alkyl of 1 to 4 carbon atoms, by —OH, by methoxy or by a mixture thereof, $R_3$ is hydrogen or alkyl of 1 to 4 carbon atoms, or $R_2$ $R_3$ together are tetramethylene, A is a direct bond or a straight or branched chain alkylene of 1 to 8 carbon atoms, $R_f$ is independently a straight or branched chain perfluoroalkyl of 1 to 14 carbon atoms, perfluoroalkyl of 2 to 6 carbon atoms substituted by perfluoroalkoxy of 2 to 6 carbon atoms, or an oligo(hexafluoropropene oxide) terminal group, n is 1 or 0, when n is 1, E is independently a branched or straight chain alkylene of 1 to 10 carbon atoms or said alkylene interrupted by one to three groups selected from the group consisting of —NR—, —O—, —S—, —SO$_2$—, —COO—, —OOC—, —CONR—, —NRCO—, —SO$_2$NR—, —NRSO$_2$—, or terminated at the $R_f$ end with —CONR— or —SO$_2$NR—, where $R_f$ is attached to the carbon or sulfur atom, and X is —S—, —O—, —SO$_2$—, —NR—, or —COO—, or when n is 0, X is a direct bond, —CONR— or —SO$_2$NR—, where $R_f$ is attached to the carbon or sulfur atom, and where R is independently hydrogen, alkyl of 1 to 6 carbon atoms or hydroxyalkyl of 2 to 6 carbon atoms, and m is 1, 2 or 3.

13. A composition according to claim 12 wherein the organic material is a synthetic polymer.

14. A composition according to claim 13 wherein the polymer is a polyolefin.

15. A composition according to claim 14 wherein the polyolefin is polypropylene.

16. A composition according to claim 12 where in formula I, II or III, $R_1$ and $R_2$ are independently methyl or a branched alkyl of 1 to 8 atoms.

17. A composition according to claim 16 wherein $R_1$ and $R_2$ are the same and are each tert-butyl.

18. A composition according to claim 12 where in formula I, II or III, $R_3$ is hydrogen or methyl.

19. A composition according to claim 18 wherein $R_3$ is hydrogen.

20. A composition according to claim 12 where in formula I, II or III, A is a direct bond or an alkylene of 1 to 3 carbon atoms.

21. A composition according to claim 20 wherein A is ethylene.

22. A composition according to claim 12 where in formula I, II or III, $R_f$ is perfluoroalkyl of 6 to 12 carbon atoms or perfluoroalkyl of 2 to 6 carbon atoms substituted by perfluoroalkoxy of 2 to 6 carbon atoms, E is alkylene of 2 to 6 carbon atoms, —CONHCH$_2$CH$_2$—, —CH$_2$CH$_2$N(CH$_3$)CH$_2$CH$_2$—, —CH$_2$CH$_2$SO$_2$NHCH$_2$CH$_2$— or —SO$_2$NHCH$_2$CH$_2$—, X is —S—, —SO$_2$— or —O—.

23. A composition according to claim 22 wherein component (b) is a compound of formula I, wherein $R_f$ is perfluoroalkyl of 6 to 12 carbon atoms, E is ethylene, and X is S.

24. A composition according to claim 12 where in formula I, m is 2 or 3.

25. A composition according to claim 12 wherein component (b) is
2,2-bis(1,1,2,2-tetrahydroperfluorooctylthiomethyl)-1,3-propanediyl bis(3,5-di-tert-butyl-4-hydroxyhydrocinnamate);
2,2-bis(1,1,2,2-tetrahydroperfluorodecylthiomethyl)-1,3-propanediyl bis(3,5-di-tert-butyl-4-hydroxyhydrocinnamate);
3-(1,1,2,2-tetrahydroperfluorooctylthio)-2,2-bis(1,1,2,2-tetrahydroperfluorooctylthiomethyl)-1-propyl 3,5-di-tert-butyl-4-hydroxyhydrocinnamate;
2,2,6,6-tetrakis(1,1,2,2-tetrahydroperfluorooctylthiomethyl)-4-oxa-1,7-heptanediyl bis(3,5-di-tert-butyl-4-hydroxyhydrocinnamate); or
7-hydroxy-2,2,6,6-tetrakis(1,1,2,2-tetrahydroperfluorooctylthiomethyl)4-oxa-1-heptyl 3,5-di-tert-butyl-4-hydroxyhydrocinnamate.

26. A composition according to claim 12 which additionally contains an effective stabilizing amount of a phenolic antioxidant other than a compound of formula I, II or III.

27. A composition according to claim 26 wherein the additional phenolic antioxidant is selected from the group consisting of n-octadecyl 3,5-di-tert-butyl-4-hydroxyhydrocinnamate, neopentanetetrayl tetrakis(3,5-di-tert-butyl-4-hydroxyhydrocinnammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)ethyl]-oxamide.

28. A composition according to claim 27 wherein the additional phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

* * * * *